United States Patent
Leeflang

(10) Patent No.: US 8,673,100 B2
(45) Date of Patent: Mar. 18, 2014

(54) STRIP LINED CATHETERS AND METHODS FOR CONSTRUCTING AND PROCESSING STRIP LINED CATHETERS

(76) Inventor: Stephen A. Leeflang, Sunnyvale, CA (US)

( * ) Notice: Subject to any disclaimer, the term of this patent is extended or adjusted under 35 U.S.C. 154(b) by 931 days.

(21) Appl. No.: 12/254,818

(22) Filed: Oct. 20, 2008

(65) Prior Publication Data

US 2009/0126862 A1 May 21, 2009

Related U.S. Application Data

(60) Provisional application No. 60/999,572, filed on Oct. 19, 2007.

(51) Int. Cl.
*B29C 47/02* (2006.01)
*B29C 53/38* (2006.01)
*B65H 81/00* (2006.01)

(52) U.S. Cl.
USPC ............ 156/171; 156/143; 156/149; 156/173; 156/184; 156/187; 156/217; 156/128; 156/244.12; 156/244.13; 156/244.18; 156/244.19; 264/209.1

(58) Field of Classification Search
USPC ......... 156/143, 149, 171, 173, 187, 217, 218, 156/244.11, 244.12, 244.13, 244.18, 156/244.19; 264/209.1
See application file for complete search history.

(56) References Cited

U.S. PATENT DOCUMENTS

| | | | |
|---|---|---|---|
| 2,805,973 A | 9/1957 | Klasing et al. | |
| 3,269,278 A | 8/1966 | Olstad | |
| 3,511,435 A | 5/1970 | Cawley et al. | |
| 3,540,959 A | 11/1970 | Houghton | |
| 3,879,516 A | 4/1975 | Wolvek | |
| 4,478,898 A | * 10/1984 | Kato | .......................... 428/36.91 |

(Continued)

FOREIGN PATENT DOCUMENTS

| | | | | |
|---|---|---|---|---|
| JP | 56109727 A | * 8/1981 | ............. | B29D 23/01 |
| WO | 9113648 | 9/1991 | | |

(Continued)

OTHER PUBLICATIONS

PCT Invitation to Pay Additional Fees and, Where Applicable, Protest Fees for PCT/US2009/061389; Applicant: Christian S. Eversull; Forms PCT/ISA/206; Dated Jul. 1992, 7 pages.

(Continued)

*Primary Examiner* — Katarzyna Wyrozebski Lee
*Assistant Examiner* — Carson Gross
(74) *Attorney, Agent, or Firm* — William A. English; Vista IP Law Group LLP

(57) ABSTRACT

Apparatus and methods are provided for making one or more tubular components of medical catheters or other tubular bodies using a strip of polymer material including a length, a width, and a first surface including a lubricious or other coating or surface modification. The strip is directed adjacent an elongate mandrel, such as beading, such that the length of the strip extends along the mandrel and the coating is disposed towards the mandrel. The strip is rolled at least partially around the mandrel such that the coating or surface modification is disposed inwardly towards the mandrel, and one or more strip-constrainment members are wrapped around the rolled strip. The directing, rolling, and wrapping steps may be substantially continuous to create one or more strip-mandrel-constrainment member subassemblies.

27 Claims, 9 Drawing Sheets

(56) References Cited

U.S. PATENT DOCUMENTS

| | | | |
|---|---|---|---|
| 4,516,972 | A | 5/1985 | Samson |
| 4,636,346 | A | 1/1987 | Gold et al. |
| 4,863,442 | A | 9/1989 | DeMello et al. |
| 5,047,045 | A | 9/1991 | Arney et al. |
| 5,176,661 | A | 1/1993 | Evard et al. |
| 5,217,440 | A | 6/1993 | Frassica |
| 5,254,107 | A | 10/1993 | Soltesz |
| 5,370,655 | A | 12/1994 | Burns |
| 5,400,785 | A | 3/1995 | Crowley |
| 5,447,497 | A | 9/1995 | Sogard et al. |
| 5,514,236 | A | 5/1996 | Avellanet et al. |
| 5,549,109 | A | 8/1996 | Samson et al. |
| 5,569,221 | A | 10/1996 | Houser et al. |
| 5,676,659 | A | 10/1997 | McGurk |
| 5,713,867 | A | 2/1998 | Morris |
| 5,735,809 | A | 4/1998 | Gorsuch |
| 5,811,043 | A | 9/1998 | Horrigan et al. |
| 5,836,926 | A | 11/1998 | Peterson et al. |
| 5,967,988 | A | 10/1999 | Briscoe et al. |
| 6,004,310 | A | 12/1999 | Bardsley et al. |
| 6,027,779 | A * | 2/2000 | Campbell et al. ......... 428/36.91 |
| 6,030,371 | A * | 2/2000 | Pursley ........................ 604/527 |
| 6,045,547 | A * | 4/2000 | Ren et al. ...................... 604/525 |
| 6,177,523 | B1 | 1/2001 | Reich et al. |
| 6,183,443 | B1 | 2/2001 | Kratoska et al. |
| 6,217,566 | B1 | 4/2001 | Ju et al. |
| 6,293,907 | B1 | 9/2001 | Axon et al. |
| 6,310,244 | B1 | 10/2001 | Tran et al. |
| 6,315,792 | B1 | 11/2001 | Armstrong et al. |
| 6,511,462 | B1 | 1/2003 | Itou et al. |
| 6,565,507 | B2 * | 5/2003 | Kamata et al. ................ 600/153 |
| 6,592,576 | B2 | 7/2003 | Andrews et al. |
| 6,669,886 | B1 | 12/2003 | Willard |
| 6,830,568 | B1 | 12/2004 | Kesten et al. |
| 6,837,890 | B1 | 1/2005 | Chludzinski et al. |
| 6,942,654 | B1 | 9/2005 | Schaefer et al. |
| 6,945,970 | B2 | 9/2005 | Pepin |
| 6,946,173 | B2 | 9/2005 | Lim et al. |
| 6,979,290 | B2 | 12/2005 | Mourlas |
| 7,188,623 | B2 | 3/2007 | Anderson et al. |
| 7,264,859 | B2 * | 9/2007 | Rouns et al. ............... 428/36.91 |
| 7,273,469 | B1 | 9/2007 | Chan et al. |
| 7,306,585 | B2 | 12/2007 | Ross |
| 7,520,950 | B2 | 4/2009 | Saadat et al. |
| 7,550,053 | B2 | 6/2009 | Leeflang et al. |
| 7,553,387 | B2 * | 6/2009 | Leeflang et al. .............. 156/217 |
| 2001/0016702 | A1 | 8/2001 | Benjamin |
| 2001/0053931 | A1 | 12/2001 | Hess et al. |
| 2002/0132076 | A1 * | 9/2002 | Stevens ........................ 428/35.8 |
| 2002/0156494 | A1 | 10/2002 | Simhambhatia et al. |
| 2003/0233115 | A1 | 12/2003 | Eversull et al. |
| 2005/0059957 | A1 | 3/2005 | Campbell et al. |
| 2005/0085841 | A1 | 4/2005 | Eversull et al. |
| 2005/0085842 | A1 | 4/2005 | Eversull et al. |
| 2005/0149104 | A1 | 7/2005 | Leeflang et al. |
| 2005/0197623 | A1 | 9/2005 | Leeflang et al. |
| 2005/0228452 | A1 | 10/2005 | Mourlas et al. |
| 2007/0074805 | A1 | 4/2007 | Leeflang et al. |
| 2007/0075452 | A1 | 4/2007 | Leeflang et al. |
| 2007/0088296 | A1 | 4/2007 | Leeflang et al. |
| 2007/0169877 | A1 | 7/2007 | Leeflang et al. |
| 2009/0126862 | A1 | 5/2009 | Leeflang et al. |
| 2009/0227962 | A1 | 9/2009 | Eversull et al. |

FOREIGN PATENT DOCUMENTS

| | | | |
|---|---|---|---|
| WO | WO 9113648 A1 * | 9/1991 | ............ A61M 25/00 |
| WO | 9620750 | 7/1996 | |
| WO | 9740880 | 11/1997 | |
| WO | 9851370 | 11/1998 | |
| WO | 9937350 | 7/1999 | |
| WO | 0107101 | 2/2001 | |
| WO | 03020353 | 3/2003 | |
| WO | 2004075961 | 9/2004 | |

OTHER PUBLICATIONS

International Publication No. WO 99/01281; Applicant: Thermon Manufacturing Company; 20 pages.

* cited by examiner

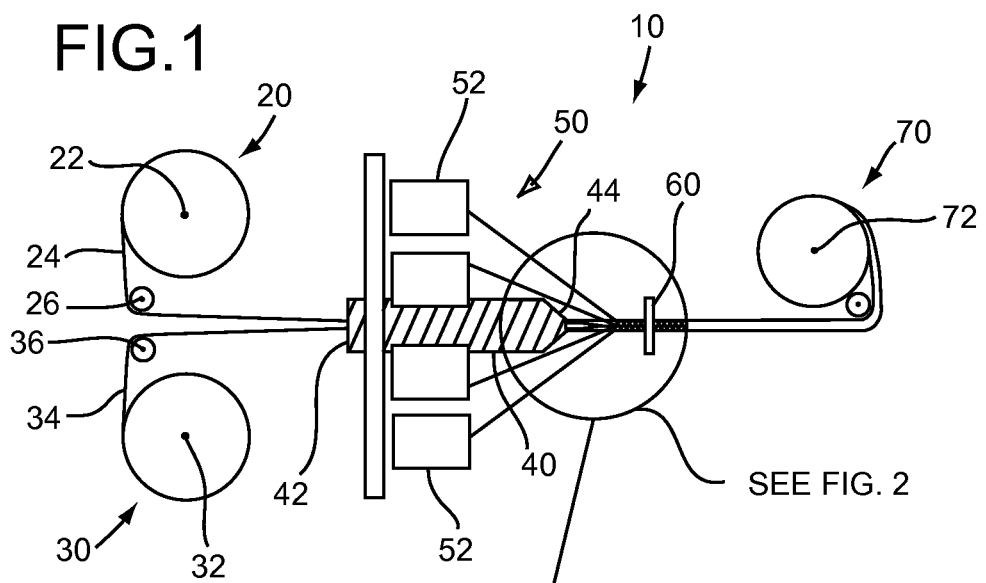
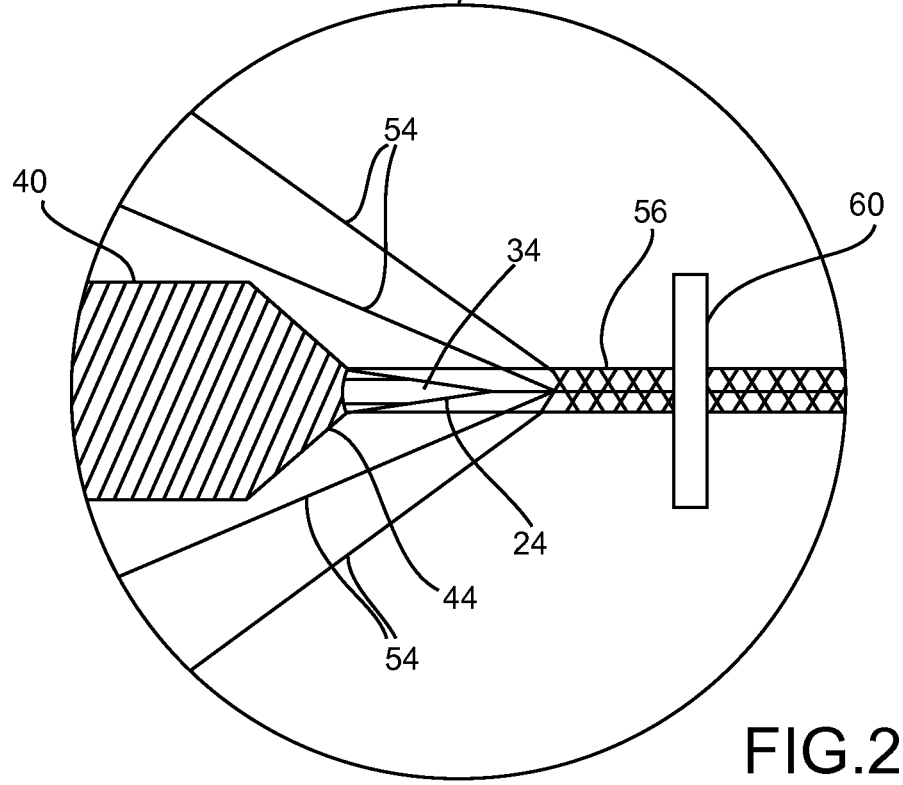

STRIP LINED CATHETERS AND METHODS FOR CONSTRUCTING AND PROCESSING STRIP LINED CATHETERS

This application claims benefit of co-pending provisional application Ser. No. 60/999,572, filed Oct. 19, 2007, the entire disclosure of which is expressly incorporated by reference herein.

FIELD OF THE INVENTION

The present invention relates generally to apparatus and methods for constructing medical catheters and more particularly to apparatus and methods for constructing strip lined catheters, for example, where incorporating the strips may offer construction flexibility, improved materials performance, and/or processing cost and quality benefits.

BACKGROUND

Devices, especially medical devices, and more especially catheters, frequently have one or more inner lumens that partially or fully extend through the device. These lumens are routinely exposed to bodily fluids or tissues and/or interact with other instruments and/or physician specified fluids unique to a given device or procedure. Given the disparate uses of these lumens and subsequent wide variety in desired performance attributes, various materials and processes have been developed and explored to impart desired performance attributes. In spite of a wide variety of materials, including specialty coatings, the processes currently known for constructing catheters including desired performance attributes are generally limited and are frequently prohibitively complicated and/or expensive. For example, applying an anti-thrombogenic coating to the inner surface of a cardiovascular catheter device or subassembly may require 1) masking undesired parts of the catheter from exposure to the coating and/or 2) special curing processes like exposure to heat or Ultraviolet ("UV") light. However, heat may be damaging to other catheter components and/or it may be difficult to expose inner surfaces of small lumens to UV light even over modest lengths. Alternatively, constructions may include lubricious liners and/or hydrophilic coatings. These tedious processes, however, routinely exact compromises that reduce the effectiveness of the materials used or applied. Furthermore, these processes do not lend themselves to batch or mass production and therefore lack the associated benefits in cost and quality.

SUMMARY

The present invention is directed to apparatus and methods for constructing medical catheters or other tubular bodies. More particularly, the present invention is directed to apparatus and methods for constructing strip lined catheters, for example, including strips that may offer construction flexibility, improved materials performance, and/or processing cost and quality benefits.

The apparatus and methods described herein may provide construction methods to 1) fabricate devices with greater flexibility in terms of materials used, 2) improve performance attributes of those materials, and/or 3) enable mass production or significantly mass production type processes (e.g., "reel to reel" processes).

In accordance with one embodiment, a method is provided for making a tubular component of a catheter using a strip of polymer material including a length, a width, and a first surface including a lubricious coating or other surface modification. The strip is directed adjacent an elongate mandrel such that the length of the strip extends along the mandrel and the first surface is disposed towards the mandrel. The strip is rolled at least partially around the mandrel such that the first surface is disposed inwardly towards the mandrel, and one or more strip-constrainment members are wrapped around the rolled strip and mandrel. The directing, rolling, and wrapping steps may be substantially continuous, e.g., from one or more source reels to one or more take-up reels, to create one or more strip-mandrel-constrainment member subassemblies.

For example, the one or more strip-mandrel-constrainment member subassemblies may be collected, e.g., wound onto a take-up reel. Alternatively, the rolled strip and mandrel wrapped by the constrainment members may be cut or otherwise separated into multiple strip-mandrel-constrainment member subassemblies, and the subassemblies may be collected in a bin or other collection area.

In addition or alternatively, the one or more strip-mandrel-constrainment member subassemblies may be encased or otherwise received in a jacket. For example, jacket material may be co-extruded around the one or more subassemblies, or the rolled strip and mandrel wrapped by the constrainment members may be separated into multiple strip-mandrel-constrainment member subassemblies; and each strip-mandrel-constrainment member subassembly may be encased in an individual jacket.

In accordance with another embodiment, a method is provided for making a catheter body that includes directing a strip of material substantially continuously from a reel to a guide to place the strip adjacent an elongate mandrel such that a length of the strip extends axially along the mandrel and a surface modification on a first surface of the strip is oriented towards the mandrel, substantially continuously rolling the strip at least partially around the mandrel such that the first surface is disposed radially inwardly towards the mandrel, and substantially continuously wrapping one or more strip-constrainment members around the rolled strip to create one or more strip-mandrel-constrainment member subassemblies. Optionally, the one or more strip-mandrel-constrainment member subassemblies may be encased in a jacket to create one or more tubular bodies.

In one embodiment, a single strip may be used to create a liner substantially surrounding a lumen of the one or more tubular bodies. In an alternative embodiment, multiple strips may be rolled around the mandrel to create a liner. The mandrel may be removed from the one or more tubular bodies, e.g., after creating the subassemblies or after incorporating the subassemblies into one or more tubular devices.

In accordance with still another embodiment, a method is provided for making a tubular component of a catheter or other tubular device. A strip of material and an elongate mandrel may be substantially simultaneously directed into a guide to align a length of the strip along a length of the mandrel and to roll the strip at least partially around the mandrel such that a first surface of the strip is disposed inwardly towards the mandrel. Optionally, the first surface and/or an opposite second surface of the strip may include a coating or other surface modification. One or more filaments or other strip-constrainment members may be wound or otherwise wrapped helically around the rolled strip as the rolled strip exits the guide to create a strip-mandrel-constrainment member subassembly. Optionally, the strip-mandrel-constrainment member subassembly may be encased in a tubular jacket.

In accordance with yet another embodiment, a method is provided for making a tubular component of a catheter or other tubular device that includes multiple lumens. A strip of material and a plurality of tubular bodies may be substantially simultaneously directed into a guide to align a length of the strip along a length of the tubular bodies and to roll the strip at least partially around the tubular bodies. One or more filaments or other strip-constrainment members may be wound or otherwise wrapped helically around the rolled strip and tubular bodies as the rolled strip exits the guide to create a subassembly. The subassembly may be encased in a tubular jacket to create a tubular component of a catheter, e.g., bonded within a sleeve or co-extruded with jacketing material to provide a desired outer finish for the tubular component.

In accordance with yet another embodiment, a method is provided for making a tubular component of a catheter or other tubular device that includes multiple lumens. A plurality of tubular bodies may be substantially simultaneously directed into a strip-constrainment mechanism to align the tubular bodies, and one or more filaments or other strip-constrainment members may be wound or otherwise wrapped helically around the tubular bodies to create a subassembly. The subassembly may be encased in a tubular jacket to create a tubular component of a catheter, e.g., bonded within a sleeve or co-extruded with jacketing material to provide a desired outer finish for the tubular component. Optionally, a mandrel may be substantially simultaneously directed into the guide with the tubular bodies. Each of the tubular bodies may be formed from a strip rolled around a mandrel that is wrapped in one or more constrainment members.

In accordance with another embodiment, an apparatus is provided for making components of catheters or other tubular bodies including one or more lumens that includes a source of strip material, the strip having a width, a length wound around the reel, and a coating or other surface modification on a first surface thereof, an elongate mandrel; a guide for directing the strip adjacent the mandrel and rolling the strip at least partially around the mandrel such that the first surface is disposed inwardly toward the mandrel; and a strip constrainment mechanism for wrapping one or more constrainment members around the rolled strip after the rolled strip exits the guide to constrain the strip around the mandrel. The apparatus may include a drive mechanism for substantially continuously directing the strip and mandrel along the guide and strip constrainment mechanism to create one or more strip-mandrel-constrainment member subassemblies.

Optionally, the apparatus may include a collection area for storing the one or more strip-mandrel-constrainment member subassemblies, e.g., a take-up reel or container. The apparatus may also include a constrainment block, e.g., for guiding the one or more strip-mandrel-constrainment member subassemblies from the constrainment mechanism to the collection area.

In addition or alternatively, the apparatus may include a co-extruder into which the one or more strip-mandrel-constrainment member subassemblies are directed. The co-extruder may include a hopper or other container of jacketing material and a die for directing the jacketing material around the one or more strip-mandrel-constrainment subassemblies to create one or more tubular bodies having a desired outer finish.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1 is a schematic of a first exemplary embodiment of an apparatus showing a process in which strip and beading are fed into a strip constrainment mechanism, e.g., including braiding or wrapping, and subsequently spooled on a take-up reel.

FIG. 2 is a detail of the strip constrainment mechanism (including braid in this illustration) of FIG. 1.

DETAILED DESCRIPTION OF THE EXEMPLARY EMBODIMENTS

Figure 3:
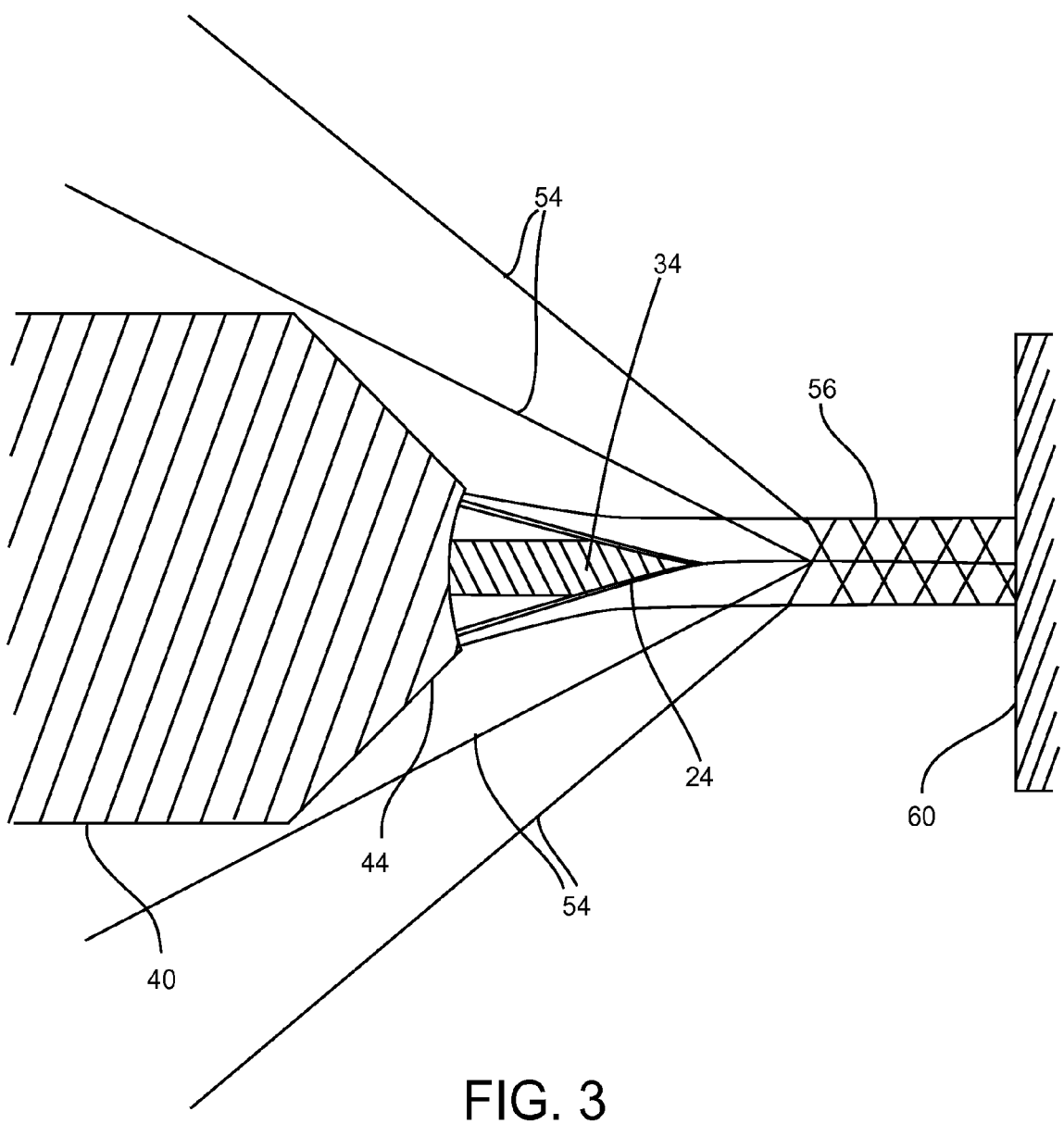
FIG. 3 is a further detail of the constrainment mechanism (including braid in this illustration) of FIG. 1, showing a strip folded around beading and subsequently constrained by one or more strip constraint members (braid in this illustration).

Turning to the drawings, FIGS. 1-3 show a first exemplary embodiment of an apparatus 10 for making tubular bodies, such as catheters and/or components for catheters or other tubular devices (not shown). Generally, the apparatus 10 described herein may allow for substantially continuous fabrication of tubular bodies, such as strip-mandrel-constrainment member subassemblies and/or catheter bodies. As used herein, "substantially continuous" means that the apparatus and/or method may operate indefinitely, i.e., to make as few as one or as many as hundreds or thousands of tubular bodies, e.g., by substantially simultaneously feeding components of the tubular bodies from sources, such as reels, through the apparatus until the sources are depleted, whereupon new source(s) may be loaded onto the apparatus and the process continued. Thus, the apparatus and methods described herein may be used to make relatively long tubular bodies, e.g., that are substantially longer than finished catheters or other tubular devices. The resulting tubular bodies may be collected, e.g., on a take-up reel or container, or may be separated into individual shorter tubular bodies that may be incorporated into individual catheters or other tubular devices, as described further below.

As shown in FIG. 1, the apparatus 10 includes one or more sources of strip material 20 and mandrel material 30, a guide 40 for directing one or more strips of the strip material and mandrel(s) adjacent one another and/or rolling the strip(s) 20 around the mandrel(s) 30, a strip constrainment mechanism 50, a constrainment block 60, and a collection area 70. In addition, the apparatus 10 (or any of the apparatus described herein) may include one or more additional components, such as drive mechanism, a cutter, a co-extruder, laminator, a tension adjuster, and the like (not shown), e.g., as described further below.

The source(s) of strip material 20 may include one or more reels 22, each carrying a strip of material 24 wound thereon. The strip of material 24 generally includes a base material, e.g., a relatively thin-walled polymer sheet having a width, a length, a first surface and a second surface opposite the first surface. Exemplary materials for the strip 24 include plastics, e.g., thermoplastics, such as polyether block amide, urethane, nylon, and the like, fluoropolymers, such as PTFE, FEP, TFE, and the like, thermoset, and thermoform plastics, such as polyimide or polyester, and the like. Alternatively, the strip 24 may be formed from thin metal sheets, such as stainless steel or Nitinol, or composite materials. The strip 24 may have a thickness between about 0.0001-0.050 inch (0.0025-1.25 mm), 0.0001-0.003 inch (0.0025-0.076 mm), or 0.0001-0.0015 inch (0.0025-0.038 mm).

Figure 11A:
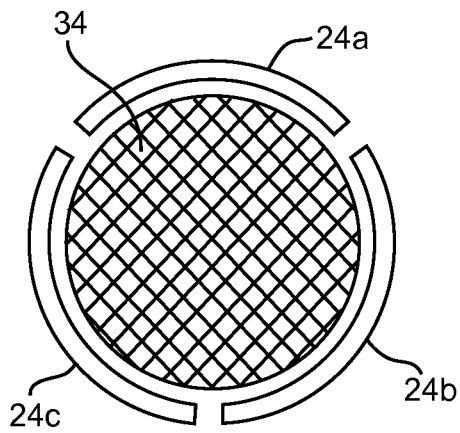
FIGS. 11A and 11B are cross-sectional views of alternative embodiments of strip-mandrel subassemblies including multiple strips wrapped around beading.
Figure 11B:
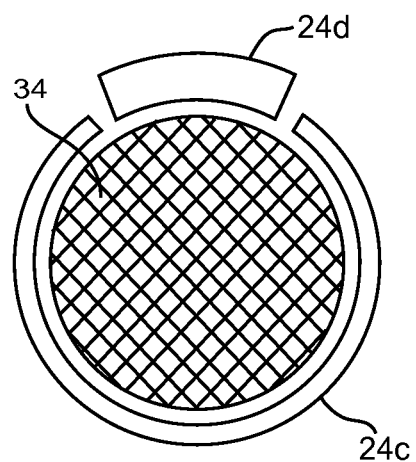
Figure 12:
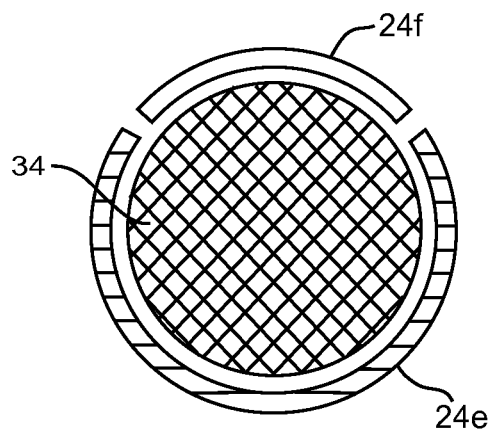
FIG. 12 is a cross-sectional view of another alternative embodiment of a strip-mandrel subassembly including multiple strips of different material properties wrapped around beading.
Figure 13A:
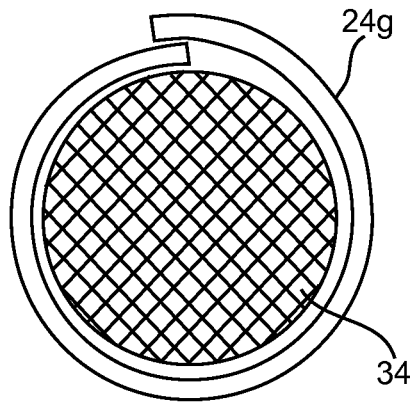
FIGS. 13A-13C are cross-sectional views of additional strip-mandrel subassemblies including overlapping strips.

The width of the strip 24 may correspond substantially to the circumference of an inner lumen of a catheter body (not shown) lined or surrounded by the strip 24, e.g., being wider or narrower than the inner lumen while the length may correspond to the length of one or more catheters or other tubular bodies or members incorporating at least a portion of the strip 24. For example, the width may be substantially the same as the circumference of the lumen such that side edges of the strip 24 abut one another or are spaced apart slightly from one another when rolled to the desired diameter, as described further below. Alternatively, the width may be slightly greater than the circumference such that the side edges overlap one another when rolled, e.g., as shown in FIG. 13A. In a further alternative, the width may be less than the circumference such that the strip 24 only partially defines a liner of a lumen of a catheter and one or more additional strips define the remainder, e.g., as shown in FIGS. 11A, 11B, and 12, and described further below.

The first surface of the strip 24 may include one or more coatings or other surface modifications, e.g., a hydrophilic and/or lubricious coating thereon (not shown). In addition or alternatively, the opposite second surface of the strip 24 may also include a coating, e.g., including a drug or other therapeutic substance, e.g., that may be released through the strip 24. In this alternative, the strip material may be at least partially porous to allow the substance to pass therethrough. In further alternatives, the first and/or second surfaces may include other surface modifications, if desired, such as etching or other texturing.

The strip 24 may be formed from a wider sheet of material that has been slit or otherwise separated into multiple strips and then wound onto reels or other carriers, such as reel 22, and the like. For example, sheets of material may be formed and treated as desired on the appropriate surface (e.g., the surface facing the beading in the case of coatings such as hydrophilic and/or lubricious coatings, or the opposite surface in the case of some drugs for proper dispersion control), and then cut into strips and loaded onto rolls. Alternatively, the strip 24 may be formed from source material, e.g., by extruding the source material, into a strip having the desired width, thickness, and length, and then a first surface of the strip 24 may be coated with one or more coatings having desired properties. Additional information on materials and methods for making sheets or strips that may be used in the apparatus and methods herein may be found in U.S. Publication Nos. 2007/0074805, published Apr. 5, 2007, and 2007/0169877, published Jul. 26, 2007. The entire disclosures of these references are expressly incorporated by reference herein.

The mandrel source 30 may include a beading supply reel 32 carrying a length of beading material 34 wound thereon, which may be pulled from the reel 32 through the apparatus 10 substantially simultaneously with the strip 24 and directed through the rest of the apparatus 10. The beading 34 may have easy release properties, e.g., allowing the strip 24 to be rolled around the beading 34 with minimal friction between the strip 24 and the beading 34, which may facilitate removing the beading 34 from within the rolled strip 24, as described further below. For example, the beading 34 may be formed from lubricious material, e.g., PTFE or other fluoropolymer, silicone-treated Acetal, PTFE-coated stainless steel, Parylene-coated stainless steel, and the like, having sufficient flexibility to allow the beading 34 to be wound onto the source reel 32 and/or onto a take-up reel (such as take-up reel 72 shown in FIG. 1) after being incorporated into a strip-mandrel-constrainment member subassembly or other tubular body. The beading 34 may be a solid or hollow wire or other cylindrical member having a diameter (or other cross-section) corresponding to the diameter of the lumen to be lined by the strip 24, e.g., between about 0.005-0.300 inch (0.125-7.5 mm), 0.014-0.092 inch (0.35-2.3 mm), or 0.014-0.045 inch (0.35-1.15 mm). Similar to the strip 24, the beading 34 may have sufficient length to construct from one up to hundreds or thousands of subassemblies in a single load.

Returning to FIG. 1 with additional reference to FIGS. 2 and 3, the guide 40 includes a housing or other structure having an inlet 42 through which the strip 24 and beading 34 may be received and a conical (or otherwise shaped) outlet 44 that directs the strip 24 to roll at least partially around the beading 34, as best seen in FIG. 3. As shown in FIG. 1, the guide 40 may direct the strip 24 and beading 34 from their respective reels 22, 32 (e.g., via one or more optional guide rollers 26, 36) to position the strip 24 adjacent the beading 34 with the first surface (e.g., the surface including the coating) oriented towards the beading 34. As the strip 24 exits the guide 40, the conical shape of the outlet 44, as well as the tension applied to the strip 24 by the apparatus 10, may cause the strip 24 to curve and then wrap or otherwise roll around the beading 34.

The strip constrainment mechanism 50 may receive the rolled strip 24 and beading 34 and constrain the strip 24 such that the strip 24 wraps substantially around the beading 34, e.g., until side edges of the strip 24 substantially abut adjacent one another, forming a substantially enclosed three hundred sixty degree (360°) liner around the beading 34. In an exemplary embodiment, the strip constrainment mechanism 50 includes a plurality of rollers, reels, spools, or other carriers 52 having fibers, wires, bands, or other filaments or constrainment members 54 wound thereon. The plurality of constrainment members 54 may be braided or otherwise wrapped, e.g., helically or otherwise circumferentially, around the rolled strip 24 as the rolled strip 24 and beading 34 passes therebetween, thereby creating a strip-mandrel-constrainment member subassembly 56, as best seen in FIGS. 2 and 3. Alternatively, the strip constrainment mechanism 50 may include other braiders or wrappers (not shown), which may wrap one or more constrainment members around the rolled strip 24 to constrain the strip 24 around the beading 34 and create the strip-mandrel-constrainment member subassembly 56.

The constrainment members 54 may be elongate, relatively small cross-section filaments, for example, stainless steel braid filaments having round or rectangular cross-sections or other geometries and/or made from various tempers. Other exemplary materials for the constrainment members 54 include other metals, such as Nitinol, copper, silver, gold, or platinum, glass, plastics, such as polyester fiber, Kevlar fiber, acrylic filament, polyimide fiber, thermoplastic materials, such as polyether block amide, urethane, nylon, and the like. Various braiding or other arrangements may be used to wrap the constrainment members 54 around the rolled strip, such as herringbone, one over one under, coiling with wire, wrapping with film, polymer, or thread, and adhesion from an encompassing strip. The constrainment members 54 may provide a reinforcing layer around the strip 54, which may provide an internal reinforcing layer in the final catheter or other tubular device, e.g., providing kink resistance, torque transmission, and/or other desired properties.

Returning to FIG. 1, the constrainment block 60 may receive the strip-mandrel-constrainment member subassembly 56 from the strip constrainment mechanism 50 and direct the strip-mandrel-constrainment member subassembly 56 to the collection area 70. The constrainment block 60 may maintain the components in proper alignment, e.g., to minimize any wandering or undesired movement of the constrainment members 54 as they are pulled from the reels 52 and/or maintain the strip 24 and beading 34 in a desired plane. Alternatively, the constrainment block 60 (or subsequent component) may at least partially bond or otherwise attach the constrainment members 54 to the rolled sheet 24. For example, the constrainment block 60 may be heated to cause the rolled strip 24 and/or constrainment members 54 to soften or partially melt, which may embed the constrainment members 54 into the rolled strip 24, or merely bond the constrainment members 54 to the outer surface of the rolled strip 24. In a further alternative, the constrainment block 60 may apply an adhesive to the outer surface of the rolled strip 24, e.g., by spraying, brushing, and the like, to bond the constrainment members 54 to the outer surface of the rolled strip 24.

As shown in FIG. 1, the collection area 70 may include a take-up reel 72 onto which the subassembly 56 may be wound. The take-up reel 72 may have a relatively large diameter compared to the diameter of the subassembly 56 such that subassembly 72 may be wound substantially continuously around the take-up reel 72 without substantial risk of kinking or buckling.

Optionally, the apparatus 10 may include one or more additional components not shown in FIGS. 1-3. For example, the apparatus 10 may include a drive mechanism (not shown) for directing the strip 24, beading 34, and/or constrainment members 54 through the apparatus 10 and/or maintaining desired tension on these components to ensure that the strip 24 is properly rolled and constrained around the beading 34. For example, a pair of rollers or other pull mechanism may be positioned along the path taken by the strip 24 and beading 34, e.g., after the constrainment block 60, similar to rollers 80' shown in FIG. 4. One or both rollers 80' may be coupled to a motor (not shown) for spinning the roller(s) 80' at a desired speed and tension to pull the strip 24, beading 34, and/or constrainment members 54 through the constrainment block 60. In addition or alternatively, a motor (not shown) may be coupled to the take-up reel 72 for pulling the subassembly 56 around the take-up reel 72, e.g., in addition to or instead of the pull mechanism.

In addition, the apparatus 10 may include one or more tension adjustment mechanisms for adjusting the tension applied to the components of the subassembly 56, e.g., to ensure proper wrapping the strip 24 around the beading 34 and/or tighten or loosen the constrainment members 54 around the rolled strip 24. For example, one or more components and/or the subassembly 56 may pass through an arrangement of pulleys (not shown) that may be selectively positioned to adjust tension.

Optionally, the apparatus 10 may include a cutter or other tool (not shown) located after the constrainment block 60 for separating the subassembly 56 into a plurality of tubular bodies, if desired. In this alternative, the individual tubular bodies may be subjected to further processing individually, e.g., using a lay-up process such as that shown in FIG. 9, and not wound onto the take-up reel 72. For example, the apparatus 10 may include drive rollers and a cutter (not shown, but similar to that shown in FIG. 6), which may periodically cut or otherwise separate the subassembly 56 into individual strip-mandrel-constrainment member subassemblies 156, which may be received in a collection area 170, as shown in FIG. 9.

Figure 9:
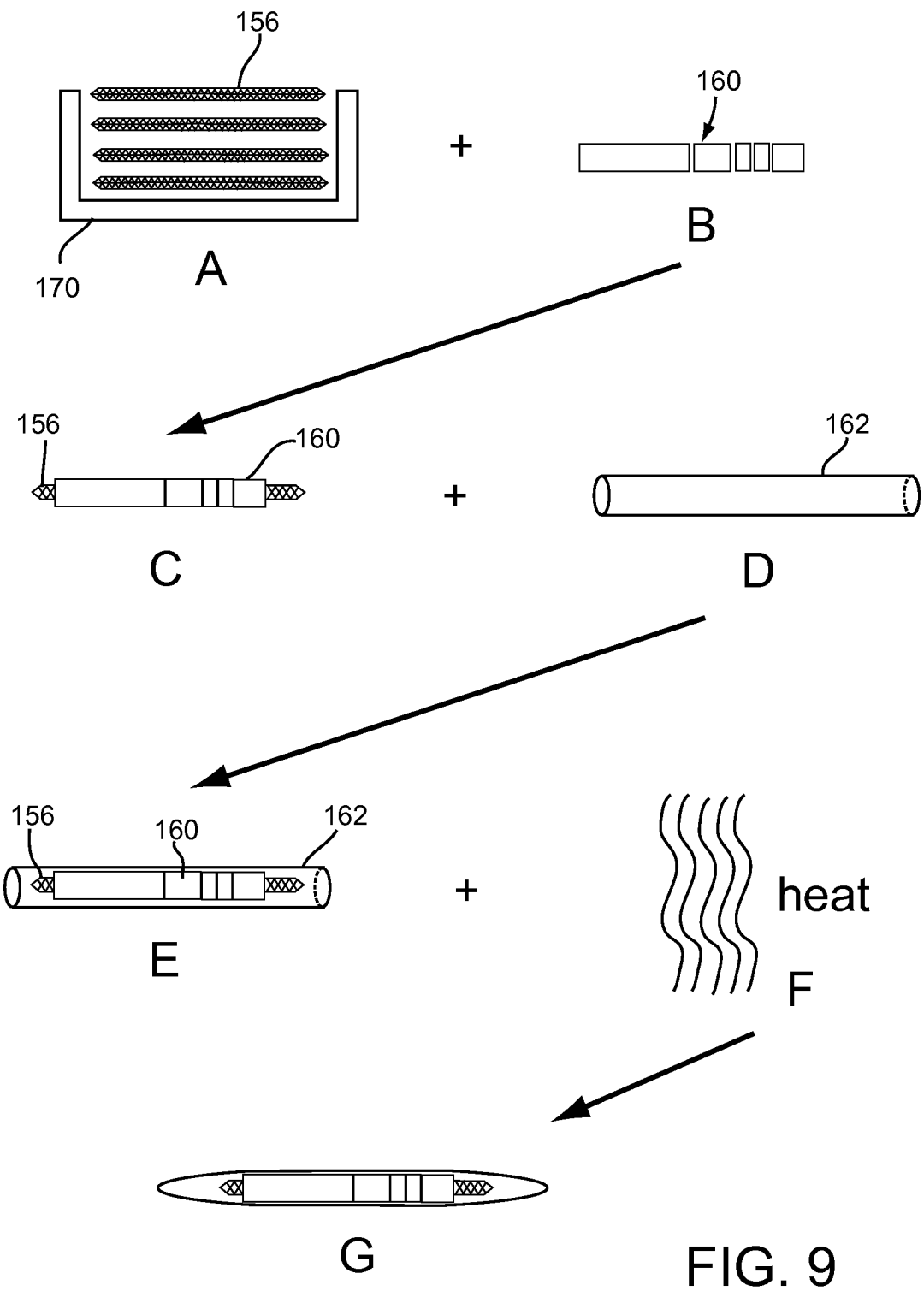
FIG. 9 is a schematic showing an alternative "jacketing process" where individual pieces of jacketing material are individually placed over strip-mandrel-constrainment subassemblies and subsequently integrated through a heating or bonding process and subjected to external compression.

For example, as shown in FIG. 9 at A, a plurality of separate strip-mandrel-constrainment member subassemblies 156 are shown in a storage container 170. At B, one or more tubular segments 160 may be formed or otherwise provided that are intended to become an outer layer of a catheter or other tubular device. At C, the tubular segments 160 may be disposed around one of the subassemblies 156. At D and E, a section of heat shrink tubing or other tubular material 162 may be provided and advanced over the tubular segments 160 and subassembly 156. At F, heat may be applied, e.g., to cause the tubing 162 to shrink and compress the tubular segments 160, while heating the tubular segments 160 and/or the subassembly 156. This may cause material of the tubular segments 160 and/or subassembly 156 to soften, partially melt, or otherwise flow to bond the tubular segments 160 around the subassembly 156, as shown at G. Thereafter, the tubing 162 and the beading (not shown) may be removed to provide a tubular device. Alternatively, additional lay-up methods for creating tubular devices may be used, such as those disclosed in the references incorporated by reference above.

Figure 5:
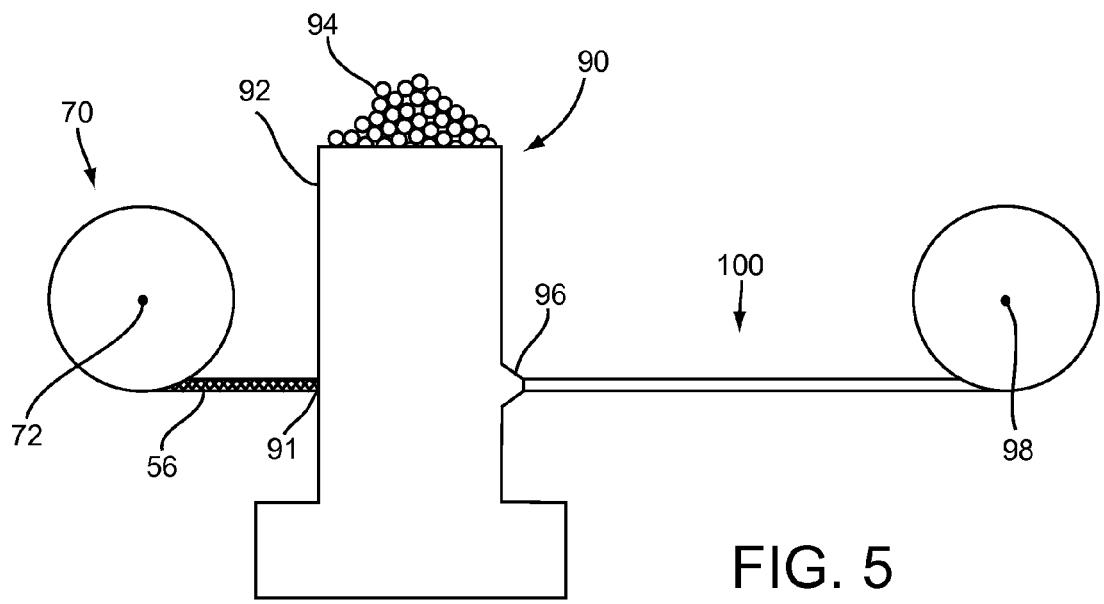
FIG. 5 is a schematic of another apparatus for feeding strip-beading-constrainment subassemblies into a co-extrusion or "jacketing" process and onto a take-up reel.

Returning to FIG. 5, the take-up reel 72 may facilitate further processing of strip-mandrel-constrainment member subassemblies 56, e.g., in a further substantially continuous process, rather than an individual lay-up process such as that just described. For example, as shown in FIG. 5, the take-up reel 72 carrying a continuous length of the strip-mandrel-constrainment member subassembly 56 may be moved from the apparatus 10 to a co-extruder 90 for jacketing the subassembly 56. Alternatively, the take-up reel 72 may be used as a source reel in other apparatus, e.g., for making multiple lumen tubular bodies, as described further below. In a further alternative, the co-extruder 90 may be placed in line after the constrainment block 60 of FIG. 1 before the collection area 70.

As shown in FIG. 5, the co-extruder 90 includes a hopper or other container 92 of jacketing material 94, which may be fed to a die 96. For example, the co-extruder 90 may include an internal chamber with an auger or other mechanism (not shown) for directing the jacketing material from the hopper 92 towards the die 96. The subassembly 56 may be fed through an inlet 91 into the co-extruder 90 and out through the die 96 such that the jacketing material may be extruded through the die 96 around the subassembly 56.

For thermoplastic or other flowable materials, a heater (not shown) within the co-extruder 90 may melt or otherwise soften the jacketing material to allow the jacketing material to flow through the die 96 around the subassembly 56. Alternatively, the jacketing material may be a thermoset plastic or other material such that components of the jacketing material may be delivered into the co-extruder 90, e.g., as a liquid, powder, and the like, and mixed to form a slurry that is delivered to the die 96 around the subassembly 56. The components may chemically or otherwise react with one another to form a solid jacket once cured. Exemplary materials for the jacketing material include plastics, e.g., thermoplastics, such as polyether block amide, nylon, or urethanes, thermoset plastics, metals, or composite materials.

The die 96 may include one or more plates defining an opening therethrough (not shown) that may create one or more tubular bodies 100 as the jacketed subassembly exits the co-extruder 90. For example, the die 96 may have a circular opening (not shown) having a diameter corresponding to a desired finished diameter of the tubular bodies 100. The die 96 may be interchangeable with other dies such that various size or configuration tubular bodies 100 may be created, as desired.

As shown in FIG. 5, a single continuous tubular body 100 is created using the co-extruder 90. The co-extrusion (or other jacketing process) may substantially simultaneously both seal, weld, or otherwise, connect the internal strip to the surrounding constraint members and jacketing material and provide a smooth external surface for the tubular body 100. In an exemplary embodiment, the jacketing-constrainment member-strip liner sandwich may provide a single composite with desirable properties, such as kink resistance and torque transmission. The tubular body 100 may be directed to a storage area, such as a storage reel 98, for subsequent further processing, as desired. Optionally, the tubular body 100 may be directed through additional components before being wound onto the storage reel 98. For example, the tubular body 100 may pass through a blower, an environmental chamber, or other device (not shown) to cool and/or accelerate or otherwise control curing of the jacketing material.

Figure 6:
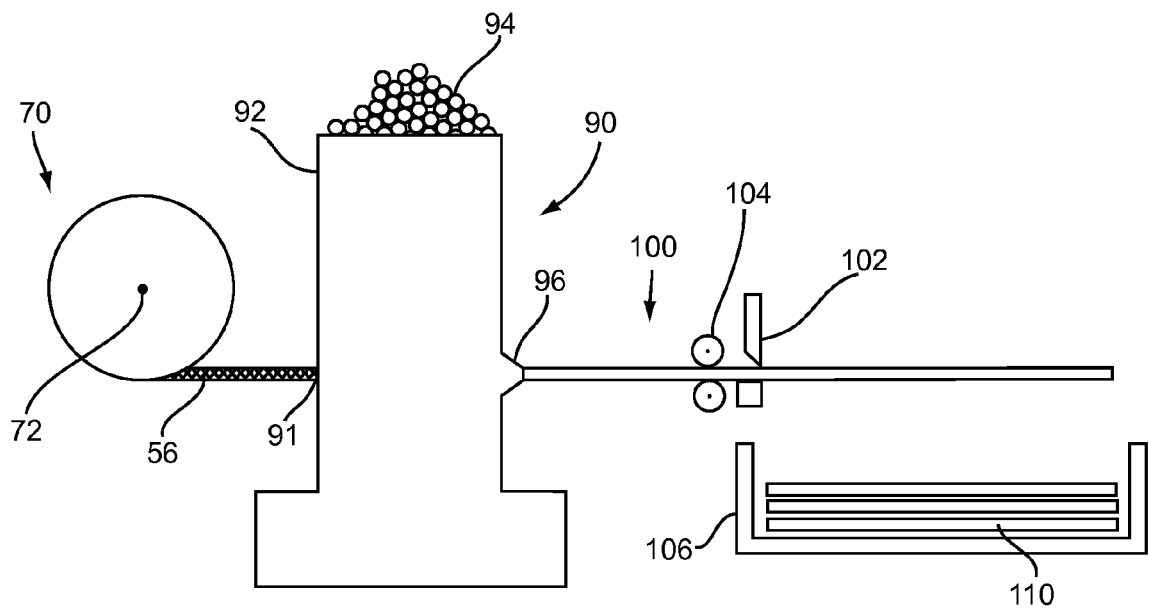
FIG. 6 is a schematic of an alternative apparatus to that shown in FIG. 5 where pieces are cut to length and gathered instead of spooled on a take-up reel.

Alternatively, as shown in FIG. 6, instead of winding the tubular body 100 on a storage reel 98, a cutter 102 may be provided that cuts or otherwise separates the tubular body 100 into multiple individual tubular bodies 110. Optionally, a drive mechanism 104 may also be provided for pushing the tubular body 100 into the cutter 102. The individual tubular bodies 110 may be received within a container 106 for subsequent processing and/or incorporation into individual catheters or other tubular devices.

Figure 4:
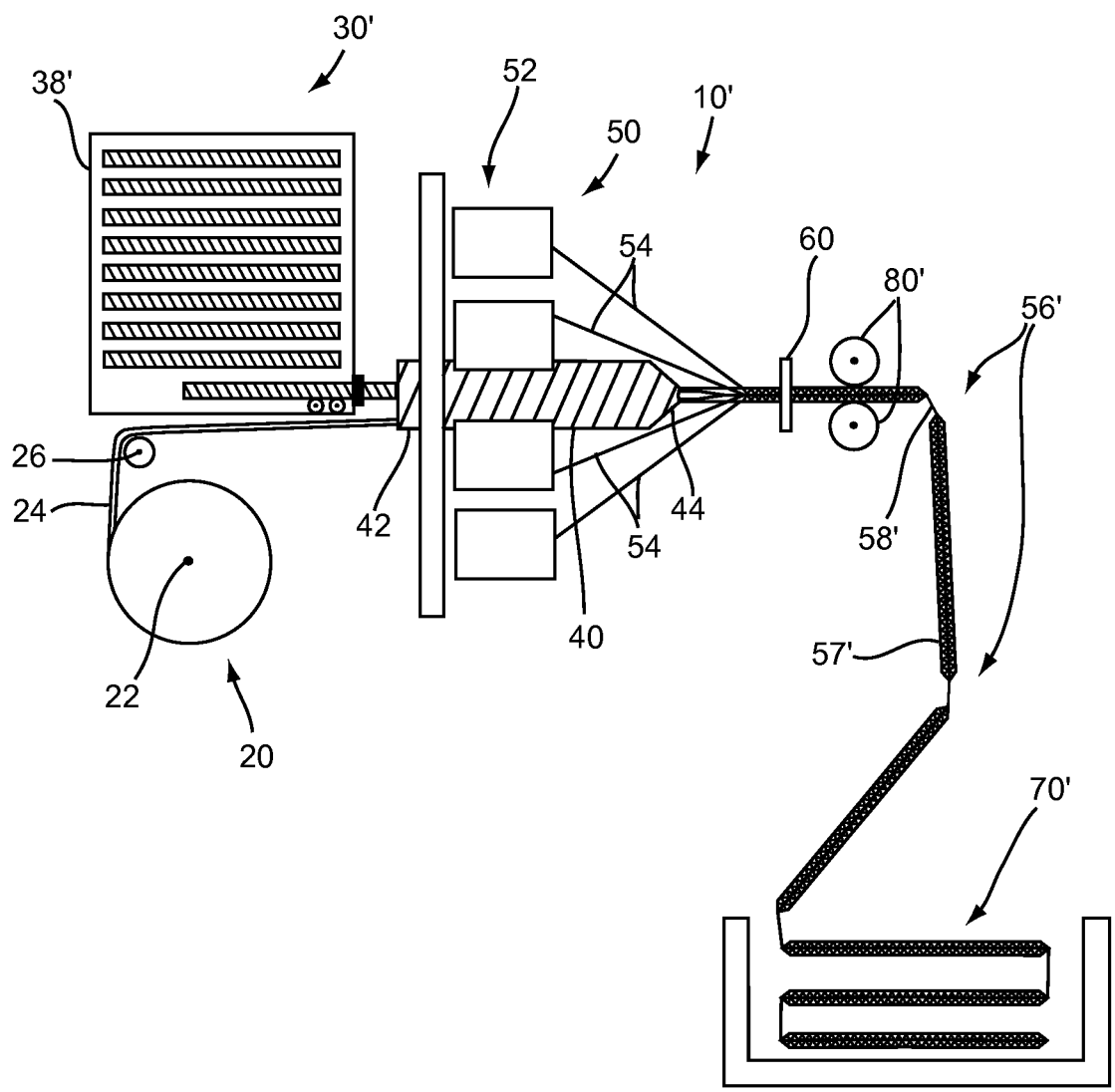
FIG. 4 is a schematic of another embodiment of an apparatus showing individual mandrels or sections of beading being fed into a guide and strip constrainment mechanism with an associated pull mechanism and collection area.

Turning to FIG. 4, an alternative embodiment of an apparatus 10' is shown that generally includes a source of strip material 20, a guide 40, a strip constraint mechanism 50, a constraint block 60, and a drive mechanism 80, which may be similar to those described above for the previous embodiments. Unlike the previous embodiments, a mandrel source 30' is provided that includes individual sections of beading or mandrels 34' with easy release properties, e.g., similar to the beading 34 described above except relatively shorter. In this embodiment, however, the beading 34' may be flexible, e.g., to allow collection on a take-up reel (not shown) or may be substantially rigid.

The beading 34' may be provided in a hopper or other container 38,' which may include a set of rollers 39' coupled to a motor or other mechanism (not shown) for directing individual lengths of beading 34' successively out of the container 38.' Thus, the individual sections of beading 34' may be automatically fed into the inlet 42 of the guide 40 to dispose the beading 34' adjacent the strip 24 and allow the strip 24 to be rolled around the beading 34.' Alternatively, the lengths of beading 34' may be fed manually or using other automated processes to direct the beading 34' into the guide 40 in successive lengths, e.g., with a relatively small distance between each length of beading 34.'

The strip 24 and lengths of beading 34' may be directed from the outlet 44 of the guide 40, wrapped by constraint members 54 of the strip constraint mechanism 50, and directed through the constraint block 60 to create strip-mandrel-constraint member subassemblies 56,' generally similar to the previous embodiments. Unlike the previous embodiments, the subassemblies 56' include individual sections of beading wrapped by the strip and constraint members 57,' which are spaced apart but connected via the continuous strip and constraint members 58' between adjacent lengths of beading. The drive mechanism 80' may pull the components of the subassemblies 56' through the apparatus 10' and into a collection area 70.' In this alternative, rather than a take-up reel, the subassemblies 56' are directed into a bin or other container 70' such that the subassemblies remain connected to one another to facilitate further processing. The resulting subassemblies 56' may be flexible or substantially rigid, e.g., depending upon the rigidity of the beading 34' used therein. If the subassemblies 56' are sufficiently flexible, the subassemblies 56' may be wound on a take-up reel, similar to the previous embodiments.

Figure 7:
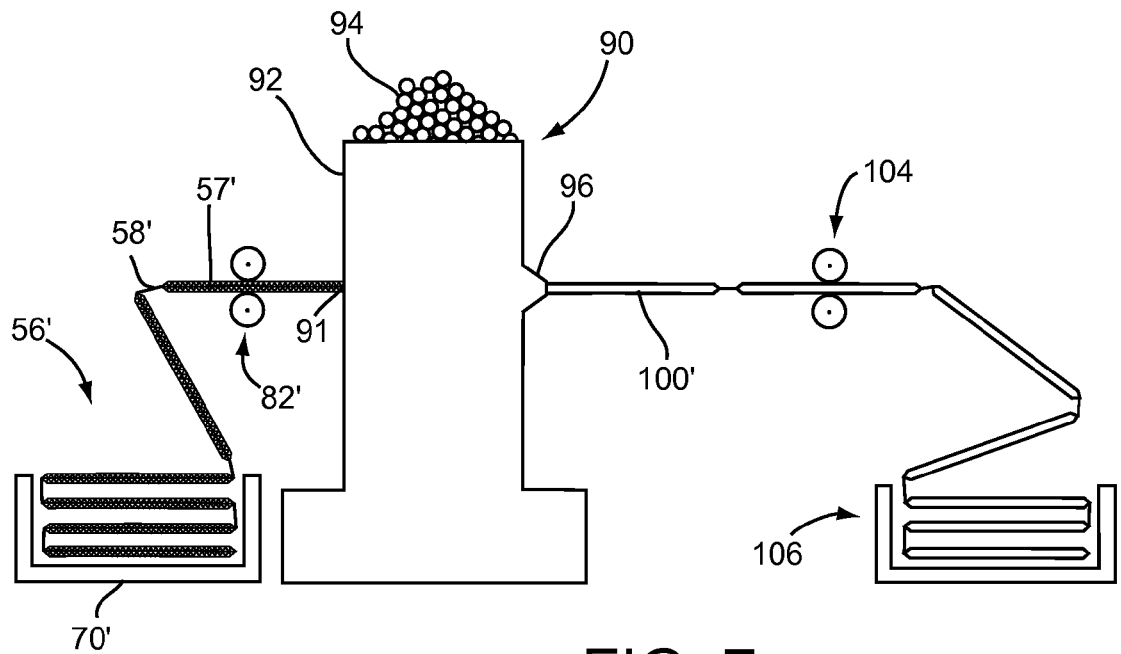
FIG. 7 is a schematic of yet another embodiment of an apparatus showing strip-mandrel-constrainment subassemblies being fed into a co-extrusion or "jacketing" process and into a collection area.

Turning to FIG. 7, a co-extruder 90 is shown for substantially continuously jacketing the subassemblies 56,' along with drive mechanisms 82,' 104 and a storage container 106. Similar to the previous embodiments, the co-extruder 90 includes a hopper 92 with jacketing material 94, an inlet 91 for receiving the subassemblies 56' and a die 96 for extruding the jacketing material around the subassemblies 56' to create one or more tubular devices 100,' similar to the previous embodiments. The strip-beading-constraint subassemblies 56' are fed from the container 70' into the co-extruder 90 and covered with the jacketing material 94. When the jacketed material has cooled sufficiently and/or cured, the tubular body 100' is collected in the storage container 106. The drive mechanism 82' may support, align, and/or guide the sections 57' of the subassemblies 56' including beading into the co-extruder 90, e.g., particularly if the beading is substantially rigid. Similarly, the drive mechanism 104 may pull the tubular body 100' from the co-extruder 90 and/or direct the tubular body 100' into the container 106.

Figure 8:
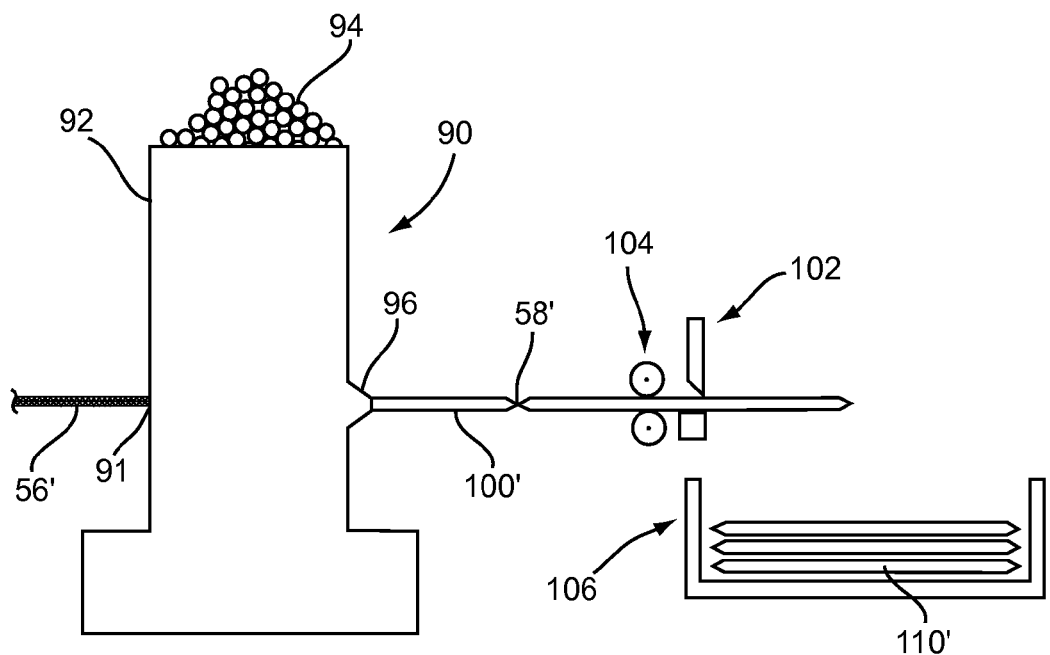
FIG. 8 is a schematic of an alternative apparatus to that shown in FIG. 7 where pieces are cut to length and gathered instead of spooled on a take-up reel.

Alternatively, as shown in FIG. 8, a cutter or other tool 102 may be provided that cuts, severs, or otherwise separates the tubular body 100' into individual tubular bodies 110.' For example, the cutter 102 may be activated to cut the strip and constraint member regions 58' between the sections having beading therein.

Figure 10A:
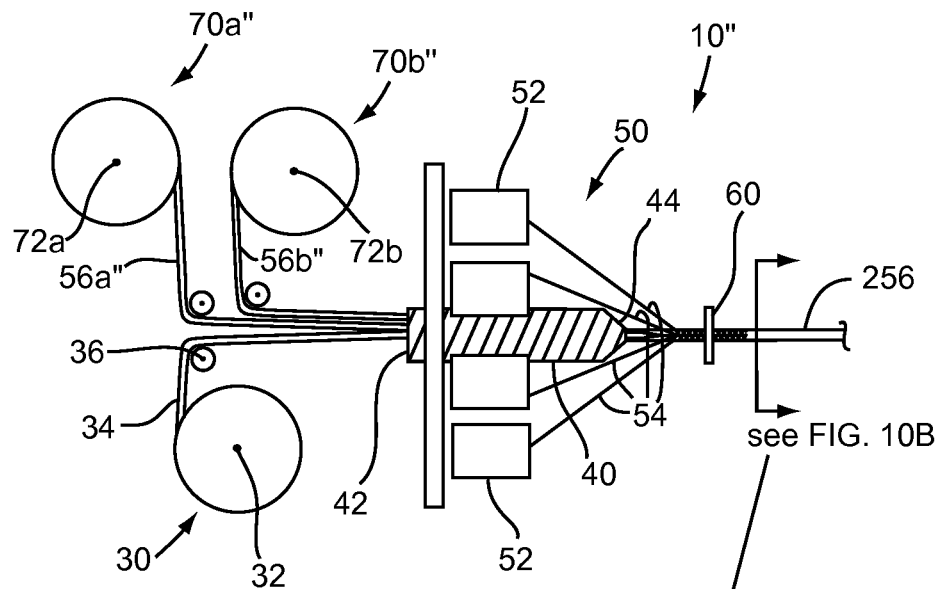
FIG. 10A is a schematic of still another embodiment of an apparatus showing an alternative process to that shown in FIG. 1 where individual strip-mandrel-constrainment subassemblies may be fed with additional beading or mandrels to form multiple lumen constructions.

Turning to FIG. 10, another embodiment of an apparatus 10" is shown for making multiple lumen subassemblies 256." Generally, similar to the previous embodiments, the apparatus 10" includes a mandrel source 30, a guide 40, a strip constraint mechanism 50, and a constraint block 60. Unlike the previous embodiments, rather than including a mandrel source, the apparatus 10" includes sources of strip-mandrel-constraint member subassemblies 70a," 70b" including a pair of take-up reels 72a," 72b" that have stripmandrel-constrainment member subassemblies 56a," 56b" wound thereon. The subassemblies 56a," 56b" may be formed using any of the materials and methods described above and may include the same or different constructions and/or sizes than each other.

Figure 10B:
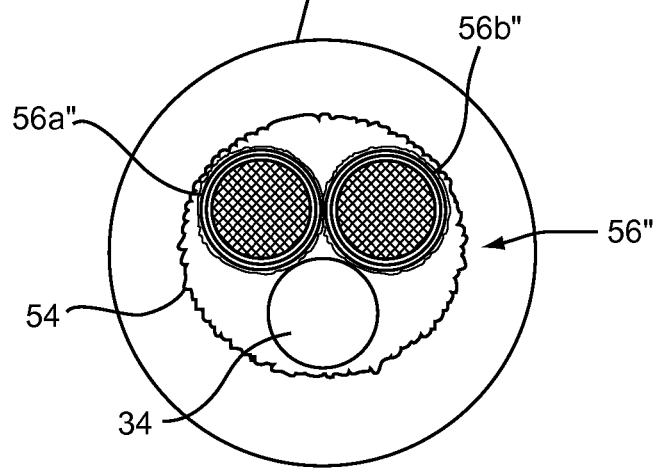
FIG. 10B is a cross-sectional view of a strip-mandrel-constrainment subassembly made using the apparatus of FIG. 10A.

The strip-mandrel-constrainment members subassemblies 56a," 56b" may be fed into the guide 40 and strip constrainment mechanism 50 substantially simultaneously with additional beading 36 such that constrainment members 54 are wrapped around the subassemblies 56a," 56b" and beading 36 to provide a multiple lumen subassembly 256" including two lumens, as shown in FIG. 10B. Alternatively, one or more additional strip-mandrel-constrainment member subassemblies (not shown) may be fed into the apparatus 10" if additional lumens are desired. In a further alternative, a strip of material (not shown) may also be fed into the apparatus 10," if desired to wrap the subassemblies 56a," 56b" and beading 36 with one or more strips of material. In still a further alternative, the subassemblies 567a," 56b" may be wrapped without additional beading.

The resulting subassemblies 256" may be collected on a take-up reel or a container (not shown) for subsequent further processing. In addition or alternatively, the subassemblies 256" may be jacketed similar to any of the previous embodiments described above, e.g., before or after being collected.

Figure 13B:
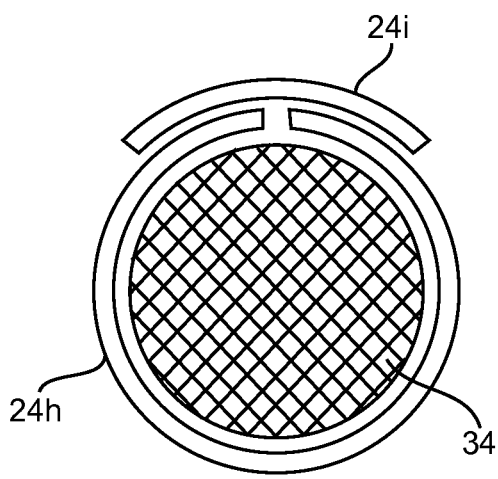
Figure 13C:
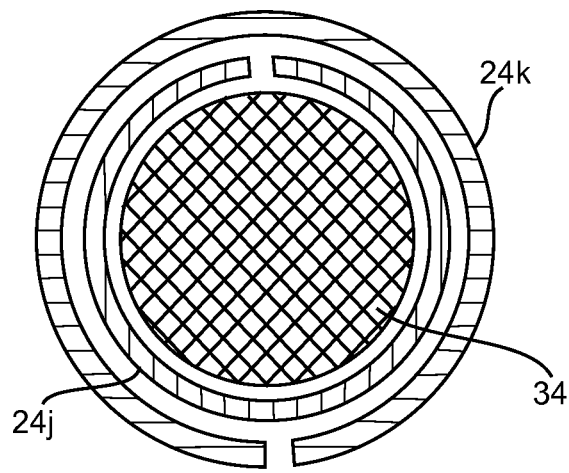

Turning to FIGS. 11-13, in yet other alternatives, multiple strips may be fed substantially simultaneously into any of the apparatus described above along with beading or other mandrel material to provide a liner having various constructions. The strips may formed from different materials and/or different sizes, and the strips may be positioned to abut or overlap one another. For example, FIG. 11A shows three different strips 24a, 24b, 24c of the same material rolled around beading 34 such that adjacent side edges of the strips 24a, 24b, 24c abut one another. FIG. 11B shows two strips 24c, 24d of the same material but having different thicknesses rolled around beading 34 with abutting side edges. FIG. 12 shows two strips 24e, 24f of different material having the same thickness rolled around beading 34 with abutting side edges. FIG. 13A shows a single strip 24g rolled around beading 34 such that side edges of the strip 24g overlap one another. FIG. 13B shows a first strip 24h rolled around beading 34 such that side edges of the first strip 24h abut one another, and a second strip 24i is rolled partially around the beading to cover the seam from the first strip 24h. FIG. 13C shows a first strip 24j rolled around beading 34 such that side edges of the first strip 24j abut one another, and a second strip 24k rolled around the beading such that side edges of the second strip 24k abut one another but are offset one hundred eighty degrees (180°) from the first strip 24j.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A method for making a tubular component of a catheter sized for introduction into a patient's body using a strip of thermoplastic polymer material including a length, a width, and a first surface comprising a surface modification, comprising:
    directing the strip adjacent an elongate mandrel such that the length of the strip extends along the mandrel and the first surface is disposed towards the mandrel;
    rolling the strip at least partially around the mandrel such that the first surface is disposed inwardly towards the mandrel; and
    wrapping a plurality of strip-constrainment members around the rolled strip,
    wherein the directing, rolling, and wrapping steps are substantially continuous to create one or more strip-mandrel-constrainment member subassemblies,
    wherein side edges of the strip remain unattached to one another when the strip is rolled around the mandrel and the strip-constrainment members are wrapped around the rolled strip.

2. The method of claim 1, further comprising collecting the one or more strip-mandrel-constrainment member subassemblies helically on a take-up reel.

3. The method of claim 1, further comprising:
    periodically separating the rolled strip and mandrel wrapped by the constrainment members into multiple strip-mandrel-constrainment member subassemblies; and
    collecting the multiple strip-mandrel-constrainment subassemblies in a collection area.

4. The method of claim 1, further comprising encasing the one or more strip-mandrel-constrainment member subassemblies in a jacket.

5. The method of claim 4, wherein the one or more strip-mandrel-constrainment member subassemblies are encased in a jacket by extruding jacket material around the one or more strip-mandrel-constrainment member subassemblies.

6. The method of claim 4, wherein encasing the one or more strip-mandrel-constrainment member subassemblies in a jacket comprises:
    separating the rolled strip and mandrel wrapped by the constrainment members into multiple strip-mandrel-constrainment member subassemblies; and
    encasing each strip-mandrel-constrainment member subassembly in an individual jacket.

7. The method of claim 6, wherein each strip-mandrel-constrainment member subassembly is encased in an individual jacket by:
    inserting a tubular member around the strip-mandrel-constrainment member subassembly; and
    heating at least one of the tubular member and the strip-mandrel-constrainment member subassembly to soften, partially melt, or flow the strip and bond the tubular member around the strip-mandrel-constrainment member subassembly.

8. The method of claim 1, wherein the strip of material is directed from a reel into a guide to place the strip adjacent to the mandrel, and wherein the guide rolls the strip at least partially around the mandrel.

9. The method of claim 1, further comprising:
separating the one or more strip-mandrel-constrainment member subassemblies into multiple tubular bodies;
directing a plurality of the tubular bodies into a guide;
directing another strip of material into the guide to roll the strip at least partially around the plurality of tubular bodies; and
wrapping one or more strip-constrainment members around the rolled strip and plurality of tubular bodies to create one or more multiple lumen tubular bodies.

10. The method of claim 1, wherein the surface modification comprises a coating on the first surface.

11. The method of claim 1, wherein side edges of the strip substantially abut one another when the strip is rolled around the mandrel.

12. The method of claim 1, wherein side edges of the strip are spaced apart from one another when the strip is rolled around the mandrel.

13. The method of claim 1, wherein side edges of the strip overlap one another when the strip is rolled around the mandrel.

14. The method of claim 1, wherein the plurality of strip-constrainment members comprise a plurality of filaments, and wherein wrapping a plurality of strip-constrainment members comprises substantially continuously braiding the plurality of filaments around the rolled strip.

15. The method of claim 1, wherein the plurality of strip-constrainment members comprise a plurality of filaments, and wherein wrapping a plurality of strip-constrainment members comprises substantially continuously braiding individual filaments around the rolled strip.

16. A method for making a catheter body sized for introduction into a patient's body, comprising:
directing a strip of thermoplastic material substantially continuously from a reel to a guide to place the strip adjacent an elongate mandrel such that a length of the strip extends axially along the mandrel and a coating on a first surface of the strip is oriented towards the mandrel;
substantially continuously rolling the strip at least partially around the mandrel such that the coating is disposed radially inwardly towards the mandrel; and
substantially continuously wrapping one or more strip-constrainment members around the rolled strip to create one or more strip-mandrel-constrainment member subassemblies; and
encasing the one or more strip-mandrel-constrainment member subassemblies in a jacket to create one or more tubular bodies,
wherein side edges of the strip remain unattached to one another when the strip is rolled around the mandrel and the strip-constrainment members are wrapped around the rolled strip.

17. The method of claim 16, further comprising collecting the one or more strip-mandrel-constrainment member subassemblies helically on a take-up reel.

18. The method of claim 16, further comprising:
periodically separating the rolled strip and mandrel wrapped by the constrainment members to create multiple strip-mandrel-constrainment member subassemblies; and
collecting the multiple strip-mandrel-constrainment subassemblies in a collection area.

19. The method of claim 16, wherein the one or more strip-mandrel-constrainment member subassemblies are encased in a jacket by extruding jacket material around the one or more strip-mandrel-constrainment member subassemblies.

20. The method of claim 16, wherein the strip comprises a first strip, the method further comprising:
directing a second strip of material substantially continuously from a reel to the guide to place the second strip adjacent the mandrel such that a length of the second strip extends axially along the mandrel and a coating on a first surface of the second strip is disposed inwardly towards the mandrel; and
substantially continuously rolling the second strip at least partially around the mandrel before wrapping the one or more strip-constrainment members around the rolled second strip.

21. The method of claim 16, wherein the strip comprises a polymer material and wherein the coating comprises a lubricious coating.

22. A method for making a tubular component of a catheter sized for introduction into a patient's body, comprising:
directing a strip of thermoplastic material and an elongate mandrel substantially simultaneously into a guide to align a length of the strip along a length of the mandrel and to roll the strip at least partially around the mandrel such that a first surface of the strip is disposed inwardly towards the mandrel; and
wrapping one or more strip-constrainment members helically around the rolled strip as the rolled strip exits the guide to create a strip-mandrel-constrainment member subassembly,
wherein side edges of the strip remain unattached to one another when the strip is rolled around the mandrel and the strip-constrainment members are wrapped around the rolled strip.

23. The method of claim 22, further comprising encasing the strip-mandrel-constrainment member subassembly in a tubular jacket.

24. The method of claim 22, wherein the first surface comprises a surface modification.

25. The method of claim 24, wherein the surface modification comprises a lubricious coating.

26. A method for making a tubular component of a catheter sized for introduction into a patient's body using a strip of thermoplastic polymer material including a length, a width, and a first surface comprising a surface modification, comprising:
directing the strip adjacent an elongate mandrel such that the length of the strip extends along the mandrel and the first surface is disposed towards the mandrel;
rolling the strip at least partially around the mandrel such that the first surface is disposed inwardly towards the mandrel; and
wrapping one or more strip-constrainment members around the rolled strip, wherein the directing, rolling, and wrapping steps are substantially continuous to create one or more strip-mandrel-constrainment member subassemblies, and
wherein the thermoplastic comprises at least one of polyether block amide, urethane, and nylon.

27. A method for making a tubular component of a catheter sized for introduction into a patient's body, comprising:
directing a strip of thermoplastic material and an elongate mandrel substantially simultaneously into a guide to align a length of the strip along a length of the mandrel and to roll the strip at least partially around the mandrel such that a first surface of the strip is disposed inwardly towards the mandrel; and wrapping one or more strip-constrainment members helically around the rolled strip as the rolled strip exits the guide to create a strip-mandrel-constrainment member subassembly, wherein side edges of the strip remain unattached to one another when the strip is rolled around the mandrel and the strip-constrainment members are wrapped around the rolled strip, and wherein the strip is formed from one of polyether block amide, urethane, and nylon.

\* \* \* \* \*